(12) United States Patent
Zhang

(10) Patent No.: US 8,495,923 B2
(45) Date of Patent: Jul. 30, 2013

(54) TESTING DEVICE FOR TESTING RIVETS

(75) Inventor: Bing-Jun Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 51 days.

(21) Appl. No.: 13/271,245

(22) Filed: Oct. 12, 2011

(65) Prior Publication Data

US 2012/0272754 A1    Nov. 1, 2012

(30) Foreign Application Priority Data

Apr. 28, 2011    (CN) .......................... 2011 1 0108710

(51) Int. Cl.
*G01N 19/00*    (2006.01)

(52) U.S. Cl.
USPC ....................................................... 73/865.9

(58) Field of Classification Search
None
See application file for complete search history.

(56) References Cited

U.S. PATENT DOCUMENTS

| | | | | |
|---|---|---|---|---|
| 2,409,589 | A | * 10/1946 | Rocheville | 30/358 |
| 2004/0092352 | A1 | * 5/2004 | Chiang | 474/160 |
| 2011/0283431 | A1 | * 11/2011 | Miller et al. | 2/10 |

* cited by examiner

*Primary Examiner* — Robert R Raevis
(74) *Attorney, Agent, or Firm* — Altis Law Group, Inc.

(57) ABSTRACT

A testing device for testing of rivets is provided. The testing device includes a first holding element and a second holding element that can be driven toward the first holding element to cooperatively define at least one hole on which at least one type of rivet can be installed. The second holding element also can be driven to separate from the first holding element to release the installed rivets for analysis.

12 Claims, 5 Drawing Sheets

US 8,495,923 B2

TESTING DEVICE FOR TESTING RIVETS

BACKGROUND

1. Technical Field

The present disclosure relates to testing devices and, particularly, to a testing device for assisting the testing of rivets.

2. Description of Related Art

Rivets are widely used to fasten two or more metal plates together. Before practical applications, it is important to install a rivet on test plates to test whether or not a specific type of rivet is suitable for a specific application. To realize this, the test plates must be drilled or punched first, which is inconvenient. In addition, after the test plates have been drilled and riveted many times, the mechanical characteristics may change, which may affect the accuracy of the test.

Therefore, it is desirable to provide a testing device, which can overcome the above-mentioned problems.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

Embodiments of the present disclosure will now be described in detail with reference to the drawings.

Figure 1:
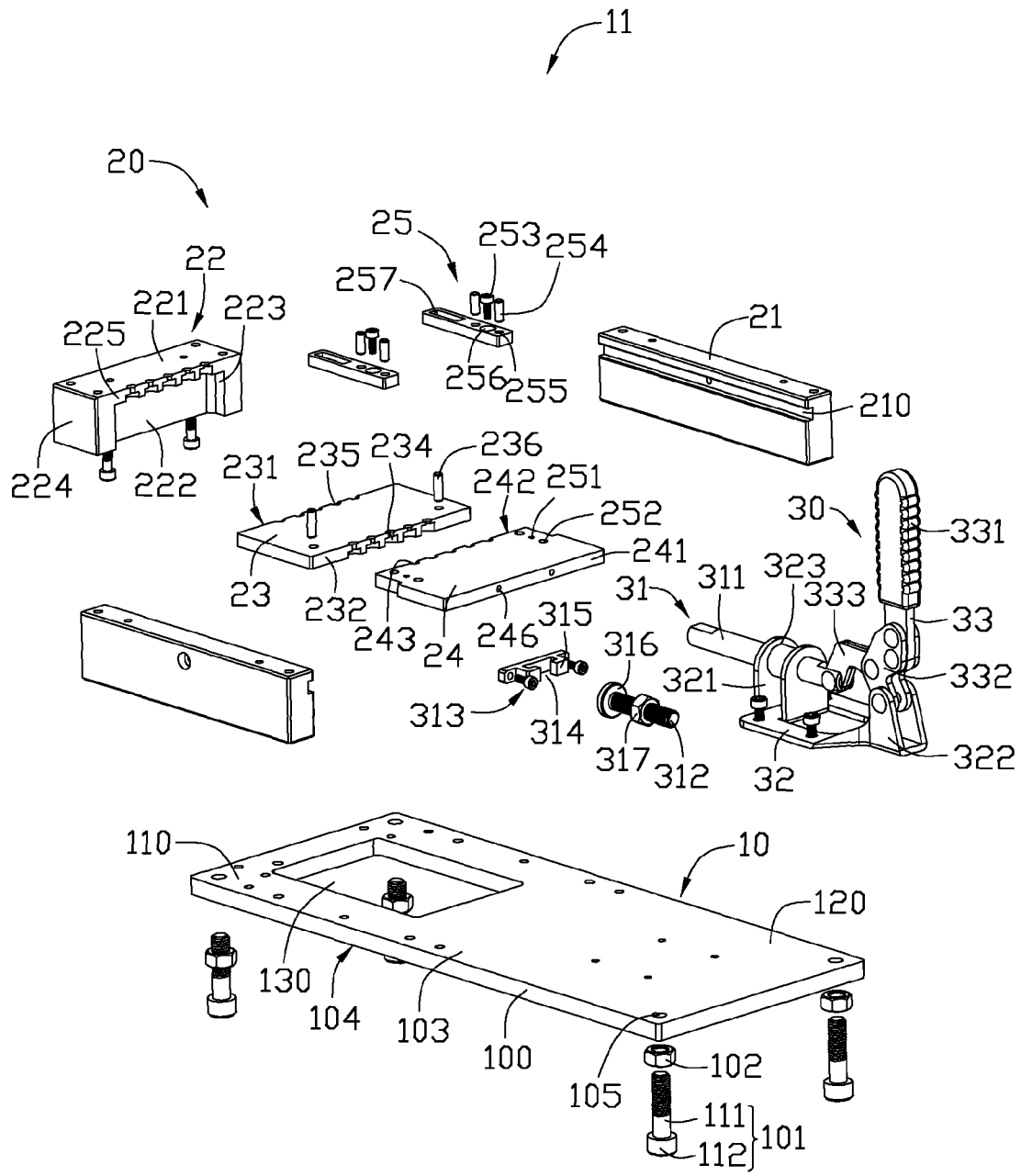
FIG. 1 is an isometric, exploded, schematic view of a testing device, according to an embodiment of the present disclosure.

Referring to FIG. 1, a test apparatus 11, according to an embodiment, includes a base 10, a holding device 20, and an operating device 30.

The base 10 includes a supporting plate 100, four bolts 101, and four nuts 102 corresponding to the bolts 101.

The supporting plate 100 is generally rectangular and includes two opposite widthwise sides 110, 120, a top surface 103, and a bottom surface 104 opposite to the top surface 103. The supporting plate 100 also defines four threaded holes 105 and an opening 130. The four threaded holes 105 are located at four corners of the top surface 103, respectively, and correspond to the bolts 101. The opening 130 extends through the top surface 103 and the bottom surface 104. The opening 130 is also rectangular and the lengthwise direction of the opening 130 is substantially parallel to that of the supporting plate 100. The opening 130 is located at the middle of the top surface 103 along the widthwise direction of the supporting plate 100 and is adjacent to the widthwise side 110 along the lengthwise direction of the supporting plate 100.

Each of the bolts 101 includes a threaded bar 111 and a head 112 located at an end of the threaded bar 111.

The holding device 20 includes a pair of rails 21, a first holding element 22, a second holding element 23, a third holding element 24, and a pair of linkage bars 25.

Each rail 21 is an elongated rectangular bar and defines a sliding groove 210 along the elongated direction in one surface.

Figure 2:
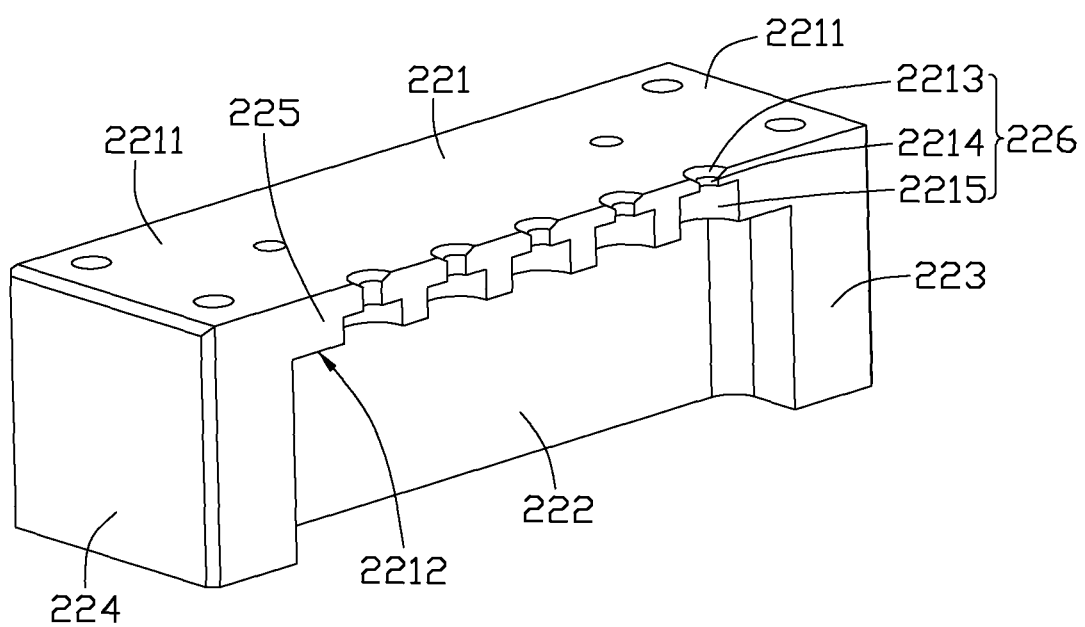
FIG. 2 is an isometric, schematic view of a first holding element of the testing device of FIG. 1.

Also referring to FIG. 2, the first holding element 22 is generally a hollow cuboid frame and includes a top plate 221, a rear sidewall 222, a left sidewall 223, and a right sidewall 224. All of the top plate 221, the rear sidewall 222, the left sidewall 223, and the right sidewall 224 are substantially rectangular. The rear sidewall 222, the left sidewall 223, and the right sidewall 224 extend downward from three edges of the top plate 221. The left sidewall 223 and the right sidewall 224 are substantially parallel with each other. The rear sidewall 222 perpendicularly connects the top plate 221, the left sidewall 223, and the right sidewall 224.

The top plate 221 includes a front surface 225 opposite to the rear sidewall 222, an upper surface 2211, and a lower surface 2212 opposite to the upper surface 2211. The front surface 225 perpendicularly connects the upper surface 2211 and the lower surface 2212. The lower surface 2212 is close to the rear sidewall 222, the left sidewall 223, and the right sidewall 224, in relative to the upper surface 2211. The top plate 221 defines a number of first semi-holes 226 in the front surface 225, extending through the upper surface 2211 and the lower surface 2212. Each first semi-hole 226 forms a first section 2213 adjacent to the upper surface 2211, a second section 2215 adjacent to the lower surface 2212, and a third section 2214 joining the first section 2213 with the second section 2215. The first sections 2213, the second sections 2214, and the third sections 2215 are different from each other in diameter and depth.

The second holding element 23 is a rectangular plate in shape and slides in the sliding grooves 210. The second holding element 23 includes a first side surface 231 and a second side surface 232 opposite to the first side surface 231. The second holding element 23 defines a number of second semi-holes 235 in the first side surface 231, corresponding to the first semi-holes 226, and a number of third semi-holes 234 in the second side surface 232. The second holding element 23 also includes two pins 236 protruding upwards from a top surface of the second holding element 23. The pins 236 are arranged in a line that is substantially parallel with the first side surface 231 and the second side surface 232.

The third holding element 24 is also a rectangular shaped plate and slides in the sliding grooves 210. The third holding element 24 includes a third side surface 241 and a fourth side surface 242 opposite to the third side surface 241. The third holding element 24 defines a number of fourth semi-holes 243 in the fourth side surface 242, corresponding to the third semi-holes 232, and two connecting holes 246 in the third side surface 241. The third holding element 24 also defines two fastening holes 251 and two positioning holes 252 in a top surface of the third holding element 24. The fastening holes 251 are arranged in a line that is substantially parallel with the third side surface 241 and the fourth side surface 242. The positioning holes 252 are also arranged in a line that is substantially parallel with the third side surface 241 and the fourth side surface 242. Each fastening hole 251 and the corresponding positioning hole 252 are arranged in a line that is substantially perpendicular to the third side surface 241 and the fourth side surface 242, and correspond to the corresponding pin 236 in position.

Each linkage bar 25 is an elongated rectangular bar and defines an elongated slot 257 at one end and two holes 255, 256 at an opposite end. Each elongated slot 257 extends along the elongated direction of the corresponding linkage bar 25 and receives the corresponding pin 236. The holes 255, 256 in each linkage bar 25 is for aligning with the corresponding fastening hole 251 and the corresponding positioning hole 252. Each linkage bar 25 also includes a fastening pin 253 and a positioning pin 254.

The operating device 30 includes a driving rod 31, a fulcrum base 32, and a handle 33.

The driving rod 31 includes a sleeve 311, a threaded rod 312, a mounting element 313, and a fastening nut 317. One end of the threaded rod 312 is for connecting to one end of the sleeve 311, and another end of the threaded rod 312 forms a circular fixing plate 316. The mounting element 313 includes a base plate 314 and two fixing bent plates 315. The fixing bent plates 215 extend upwards from the base plate 314, in parallel and bend towards each other, cooperatively defining a fixing space therebetween, which is capable of fittingly receiving the fixing plate 316. The fastening nut 317 is threadedly sleeved over the threaded rod 312.

The fulcrum base 32 includes two guiding plates 321 and a socket 322, which can be integrally formed. The guiding plates 321 are arranged in parallel and each defines a guide hole 323. The guide holes 323 are aligned with each other. The sleeve 311 is fittingly received in the guide holes 323 but is slidable in the guide holes 323.

The handle 33 includes a handle portion 331, a first crook arm 332, and a second crook arm 333. One end of the first crook arm 332 is fixedly connected to the handle portion 331 and the other end can be pivoted on the socket 322. One end of the second crook arm 333 is rotatably connected to an end of the sleeve 311 and the other end of the second crook arm 333 is rotatably connected to the first crook arm 332 generally at the middle but slightly adjacent to the end of the first crook arm 332 which is pivoted on the socket 322. The axes on which the first crook arm 332 rotates with respect to the socket 322, the second crook arm 333 rotates with respect to the first crook arm 332 and the sleeve 311 are substantially parallel with each other but are substantially perpendicular to the axial direction of the sleeve 311. As such, the handle 33 drives the sleeve 311 to move within the guiding holes 323 by operating the handle portion 331.

Figure 3:
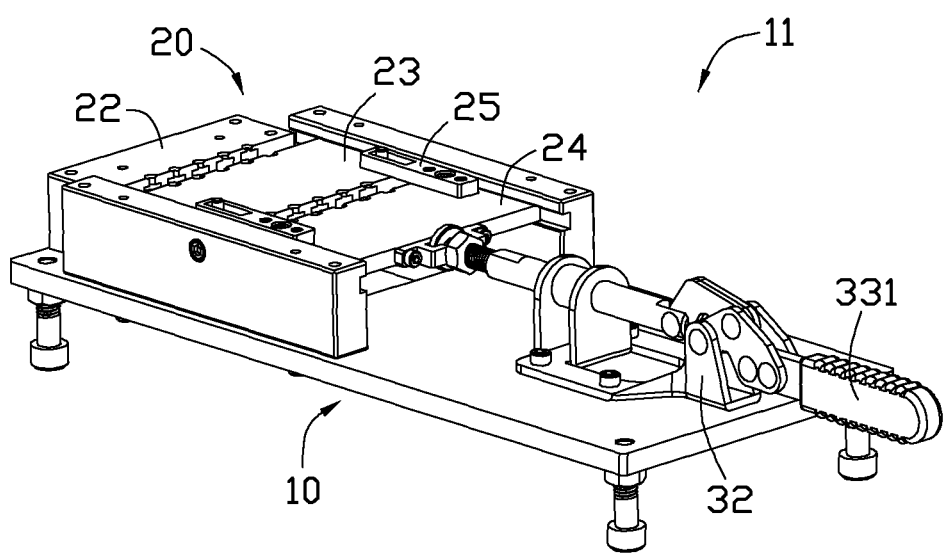
FIG. 3 is an isometric, assembled, schematic view of the testing device of FIG. 2.
Figure 4:
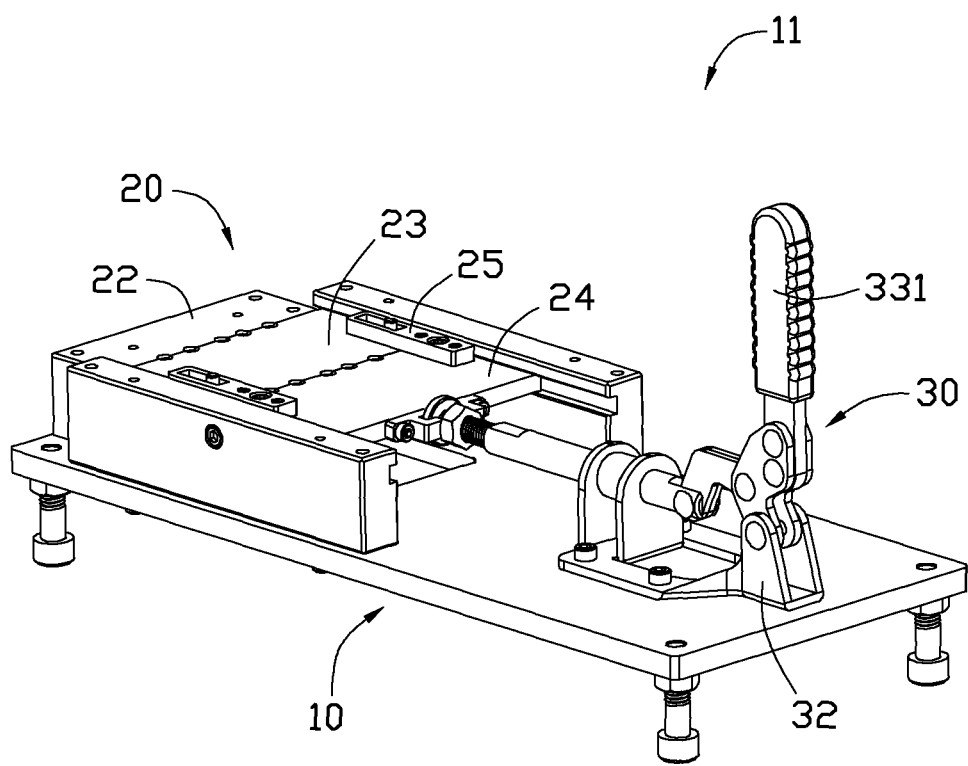
FIG. 4 is similar to FIG. 3, but showing the testing device in another operating state.
Figure 5:
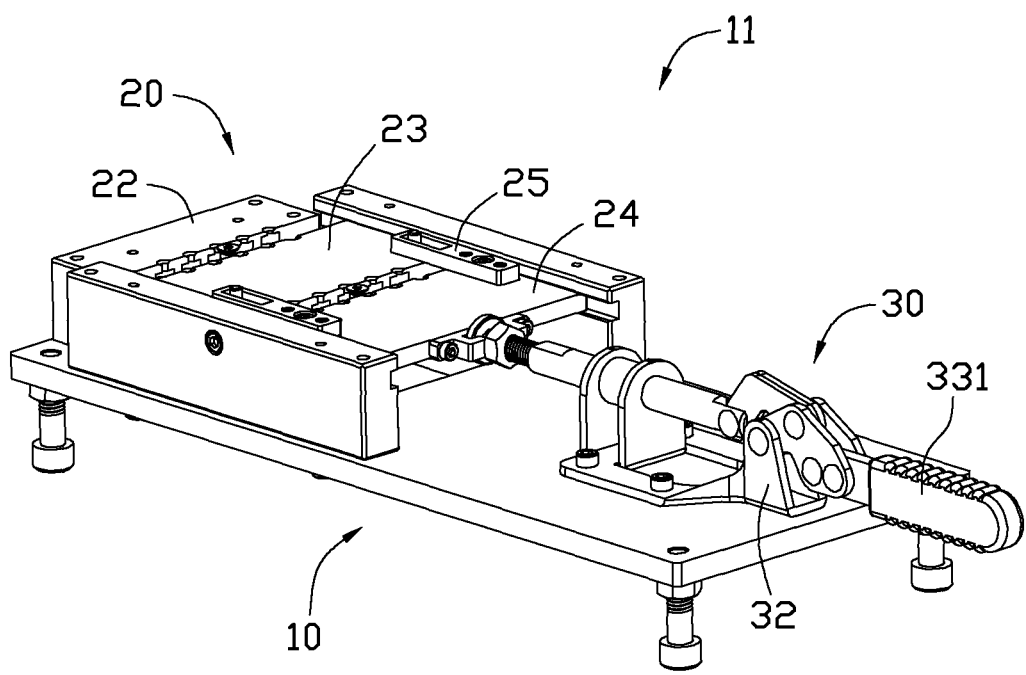
FIG. 5 is similar to FIG. 4, but showing the testing device in still another operating state.

Referring to FIG. 3, in assembly, the nuts 102 engage with the respective threaded bars 111 via an end opposite to the corresponding head 112. The threaded bars 111 are inserted into the respective threaded holes 105 using the end opposite to the corresponding head 112 via the bottom surface 104 and are threaded and engaged with the respective threaded holes 105. The lengths of the threaded bars 111 below the bottom surface 104 are adjusted until the top surface 103 is horizontally positioned. Then, the nuts 102 are screwed to abut the bottom surface 104. As such, the base 10 is assembled.

The rails 21 and the first holding element 22 are fixed to the top surface 103. The rails 21 are located at two lengthwise sides, adjacent to the widthwise side 110. The sliding grooves 210 face and align with each other. The first holding element 22 is located at the widthwise side 110 between the rails 21. The top plate 221 is located away from the top surface 103 and the front surface 225 faces away from the widthwise side 110. The second holding element 23 and the third holding element 24 slide into and are held by the sliding grooves 210. The first side surface 231 faces the front surface 225. The fourth side surface 242 faces the second side surface 232. The linkage bars 25 link the second holding element 23 and the third holding element 24. The pins 236 slidably extend through the respective sliding slots 257. The positioning pins 254 extend through the respective holes 255 and the respective positioning holes 252. The fastening pins 253 threadedly engage with the respective holes 256 and the respective holes 251.

The threaded rod 312 is connected to the sleeve 311. The mounting element 313 is connected to the third side surface 241 by fastening fasteners (not labeled) into the respective connecting holes 246. The fixing plate 316 is inserted into the fixing space defined between the fixing bent plates 315 and then the fastening nut 317 threadedly sliding towards the fixing bent plates 315 until tightly abutting against the fixing bent plates 315.

In operation, the handle portion 331 is operated to drive the second holding element 23 to abut the first holding element 22 and the third holding element 24 abuts the second holding element 23. As such, the first semi-holes 226 and the respective second semi-holes 235 cooperatively define a number of holes (not labeled) on which different types of rivets can be installed, respectively. The third semi-holes 234 and the respective fourth semi-holes 243 cooperatively define a further number of holes on which other different types of rivets can be installed, respectively. The first sections 2213 of each hole receive the factory head of the rivets, the second sections 2215 of each hole receive the buck-tail of the rivets, and the third sections 2214 of each hole receive the shaft of the rivets.

After the rivet(s) is/are installed, the handle portion 331 can be operated to separate the first holding element 22, the second holding element 23, and the third holding element 25. Then the rivet(s) falls through the opening 130 and is gathered for analyses.

In other embodiments, only three bolts 101 and three nuts 102 can be employed to position the top surface 103 horizontally. In addition, other suitable configurations of the base 10 can be employed.

In other embodiments, the second holding element 23 can be omitted, and the third holding element 24 can abut the first holding element 22 by operating the handle portion 331. The fourth semi-holes 243 and the first semi-holes 226 cooperatively define a number of holes on which different types of rivets can be installed. In addition, the number of the first semi-holes 226 and the fourth semi-holes 243 can be only one.

In other embodiments, a part or all of the first semi-holes 226, the second semi-holes 235, the third semi-holes 234, and the fourth semi-holes 243 can be the same in shape and size.

The configuration of the linkage bars 25 is not limited to this embodiment. In other embodiments, only one linkage bar 25, only one corresponding fastening pin 253, fastening hole 251, positioning pin 254, positioning hole 252, and pin 236 can be employed.

The operation device 30 is not limited in this embodiment. Other suitable configurations can be employed instead in other embodiments.

It will be understood that the above particular embodiments are shown and described by way of illustration only. The principles and the features of the present disclosure may be employed in various and numerous embodiment thereof without departing from the scope of the disclosure as claimed. The above-described embodiments illustrate the possible scope of the disclosure but do not restrict the scope of the disclosure.

What is claimed is:

1. A testing device, comprising:
   a base having a supporting surface;
   a first holding element supported on the supporting surface;
   two rails supported on the supporting surface, the first holding element comprising a front surface located between the rails, which substantially perpendicular to the supporting surface, and defining at least one first semi-hole in the front surface, which extends along a direction that is substantially perpendicular to the supporting surface, each of the rails defining a sliding groove;

a second holding element sliding in the sliding grooves of the rails, the second holding element comprising a first side surface facing and corresponding to the front surface, the second holding element defining at least one second semi-hole in the first side surface, the at least one second semi-hole corresponding to the at least one first semi-hole; and an operating device configured for driving the second holding element to move toward the first holding element until the first side surface contacts the front surface and the at least one second semi-hole together with the at least one second semi-hole forms at least one hole in which at least one specific type of rivet can be installed, the operating device being further configured for driving the second holding element to move away from the first holding element after the rivet is installed.

2. The testing device of claim 1, wherein the base comprises a supporting plate, at least three bolts, and at least three nuts, the supporting plate comprises the supporting surface and defines at least three threaded holes in the supporting surface, each of the bolts comprises a head at one end thereof and an opposite end threadedly inserting into the corresponding nut and the corresponding threaded hole from a side of the supporting plate opposite to the supporting surface, and the bolts are configured to be adjusted to position the supporting plate horizontally.

3. The testing device of claim 2, wherein the supporting plate further defines an opening in the supporting surface, which is aligned with the at least one hole to allow the installed rivet falling therethrough when the second holding element is driven to move away from the first holding element.

4. The testing device of claim 1, wherein the number of the at least one hole is more than one, and the holes are arranged along a direction that is substantially parallel to the supporting surface and are the same in shape and size to receive only one specific type of rivet.

5. The testing device of claim 1, wherein the number of the at least one hole is more than one, and the holes are arranged along a direction that is substantially parallel to the supporting surface and are different from each other in shape and size to receive different types of rivets.

6. The testing device of claim 1, wherein each hole forms a first section for receiving the factory head of the rivet, a second section for receiving the buck-tail of the rivet, and a third section for receiving the shaft of the rivet.

7. The testing device of claim 1, wherein the testing device further comprises a third holding element sliding in the sliding grooves and linked to the second holding element, the second holding element is positioned between the first holding element and the third holding element, the second holding element comprises a second side surface facing away from the first side surface, the third holding element comprises a third side surface facing the second side surface, the second holding element defines at least one third semi-hole in the second side surface, the third holding element defines at least one fourth semi-hole in the third side surface corresponding to the at least one third semi-hole, the operating device is configured for driving the third holding element to move toward the second holding element until the second side surface contacts the third side surface, the at least one third semi-hole and the at least one fourth semi-holes cooperatively forms at least one hole in which at least one type of rivet can be installed, and the operating device is also configured for driving the third holding element to move away from the second holding element.

8. The testing device of claim 7, wherein the testing device further comprises a linkage bar, the linkage bar comprises one end fixed to the third holding element and another end defining a sliding slot, the second holding element comprises a pin slidably extending through the sliding slot.

9. The testing device of claim 1, wherein the operating device comprises a driving rod, a fulcrum base, and a handle, the driving rod is slidably supported on the fulcrum base, the handle is pivoted on the fulcrum base and connected to the driving rod.

10. The testing device of claim 9, wherein the driving rod comprises a sleeve, a threaded rod, a mounting element, and a fastening nut, one end of the threaded rod connects to one end of the sleeve, and another end of the threaded rod comprises a circular fixing plate, the mounting element comprising a base plate and two fixing bent plates, the fixing bent plates extend from the base plate and are parallel with each other, the fixing bent plates are bent toward each other at distal ends thereof to cooperatively define a fixing space therebetween, the fixing plate is received in the fixing space, and the fastening nut threadedly engages with the threaded rod and tightly abuts the fixing bent plates.

11. The testing device of claim 10, wherein the fulcrum base comprises two guiding plates and a socket, the guiding plates are supported by the socket and arranged in parallel, each guiding plate defines a guiding hole, the guiding holes are aligned with each other, the sleeve is fittingly received in the guiding holes but is slidable in the guiding holes, and the handle is pivoted on the socket.

12. The testing device of claim 11, wherein the handle comprises a handle portion, a first crook arm, and a second crook arm, one end of the first crook arm is fixedly connected to the handle portion and another end is pivoted on the socket, one end of the second crook arm is rotatably connected to an end of the sleeve and another end of the second crook arm is rotatably connected to the first crook arm generally at the middle but slightly adjacent to the end of the first crook arm pivoted on the socket, axes on which the first crook arm rotates with respect to the socket, the second crook arm rotates with respect to the first crook arm and the sleeve are substantially parallel with each other but are substantially perpendicular to an axial direction of the sleeve.

* * * * *